United States Patent
McMillan et al.

[11] Patent Number: 6,026,816
[45] Date of Patent: Feb. 22, 2000

[54] METHOD OF TREATING SLEEP-DISORDERED BREATHING SYNDROMES

[75] Inventors: Kathleen McMillan, Concord; James C. Hsia, Weston; Stanley M. Shapshay, Boston; Anthony J. Durkin, Watertown, all of Mass.

[73] Assignees: Candela Corporation, Wayland; New England Medical Center Hospitals, Inc., Boston, both of Mass.

[21] Appl. No.: 09/010,704

[22] Filed: Jan. 22, 1998

[51] Int. Cl.⁷ .................................................. A61B 19/00
[52] U.S. Cl. ................................................ 128/898; 606/9
[58] Field of Search ............................. 128/898; 604/22; 606/1, 9, 13–16, 27–29, 32–40, 41–45, 46–52

[56] References Cited

U.S. PATENT DOCUMENTS

| | | | |
|---|---|---|---|
| 5,674,191 | 10/1997 | Edwards et al. | 604/22 |
| 5,810,801 | 9/1998 | Anderson et al. | 606/9 |
| 5,814,040 | 9/1998 | Nelson et al. | 606/9 |
| 5,820,626 | 10/1998 | Baumgardner | 606/13 |

FOREIGN PATENT DOCUMENTS

WO 97/37723  10/1997  WIPO.

*Primary Examiner*—Mickey Yu
*Assistant Examiner*—Kelly O'Hara
*Attorney, Agent, or Firm*—Testa, Hurwitz & Thibeault, LLP

[57] ABSTRACT

A method for treating sleep-disordered breathing syndromes, for example, snoring in a mammal. The method involves applying energy, for example, energy from laser light, to a preselected region of soft palate tissue in the mammal in an amount and duration sufficient to induce thermal injury to subepithelial tissue in the preselected region of soft palate tissue while minimizing thermal injury to epithelial tissue in the preselected region of soft palate tissue. Thermal injury of the subepithelial tissue results in stiffening of the preselected region of soft palate tissue thereby ameliorating the symptoms of the sleep-disordered breathing syndrome.

20 Claims, 4 Drawing Sheets

METHOD OF TREATING SLEEP-DISORDERED BREATHING SYNDROMES

The U.S. Government may have certain rights in this invention by virtue of grant number R43 HL-56472-01 funded by the National Institutes of Health.

FIELD OF THE INVENTION

The invention relates generally to a non-invasive method for treating sleep-disordered breathing syndromes. More specifically, the invention relates to a method for inducing stiffening and/or shrinkage of the soft palate in a mammal for reducing snoring or other sleep-disordered breathing syndromes.

BACKGROUND OF THE INVENTION

Snoring is a common disorder which occurs in a variety of sleep-disordered breathing syndromes ranging in severity from simple snoring without apnea to upper airway resistance syndrome (UARS) and obstructive sleep apnea syndrome (OSAS) (Utley et al. (1997) *Laryngoscope* 107:726–734). A recent survey reported that 40% of the general population snore regularly (Ohayon et al. (1997) *B.M.J.* 314:860–863). Although social dysfunction often prompts snorers to seek treatment, even simple snoring without apnea is being increasingly recognized as having a negative effect on the snorer's well-being. For example, snoring disrupts sleep continuity, is associated with daytime sleepiness (Breslau et al. (1997) *Am. J. Public Health* 87:1649–1653; and Stradling et al. (1991) *Thorax* 46:807–810), and increases the risk of automobile accidents (Maycock (1996) *J. Sleep Res.* 5:229–37). Furthermore, non-apneic snoring has been implicated in the development of hypertension (Guilleminault et al. (1996) *Chest* 109:901–8; Lofaso et al. (1996) *Chest* 109:896–900). Also, regular snoring has been reported to be a significant risk factor for stroke (Spriggs et al. (1992) *Neurol. Res.* 14:94–96).

In recent years, treatment of snoring and sleep apnea by laser-assisted uvulopalatoplasty (LAUP) has become one of the most commonly performed medical laser procedures. The popularity of this procedure is believed to result, in part, from the prevalence of sleep-disordered breathing syndromes and by the fact that the procedure may be performed in an office setting with the patient under local anesthesia (Kamami (1994) *J. Otolaryncol.* 23:395–398; Hanada et al. (1996) *Laryngoscope* 106:1531–1533, Walker et al., (1995) *Laryngoscope* 105:938–943; and Wareing et al., (1996) *J. Laryngol Otol.* 110:232–236). LAUP was developed as a less radical alternative to uvulopalatopharyngoplasty (UPPP), a procedure in which oropharyngeal tissue is removed by surgical excision of excessive soft tissue that comprises the free margin of the soft palate, uvula, and lateral pharyngeal wall (Croft et al., (1990) *Laryngol. Otol.* 104:871–875; Friberg et al. (1995) *Laryngoscope* 105:519–522). UPPP typically is performed under general anesthesia. However, since both LAUP and UPPP rely on cutting the palate, neither is free from risk of impairing normal palate, and neither is free from risk of impairing normal palate function thereby allowing potential liquid regurgitation and hypernasal voice. Furthermore, postoperative pain apparently is severe for both UPPP and LAUP procedures.

In a new approach for treating snoring, a central longitudinal strip of mucosa is removed from the soft palate by use of a laser (Ellis et al. (1993) *Ann. Roy. Coll. Surg. Engl.* 75:296–290; and Ellis et al. (1994) *Clin. Otolaryngol.* 19:350–351). The objective of this procedure, also performed under general anesthesia but less radical than UPPP, is to induce fibrosis so as to stiffen the soft palate. Stiffening the soft palate may reduce snoring without the risk of impaired normal palate function associated with shortening the palate as in LAUP and UPPP. Air flow and vibration tests using a mechanical model simulating the palate and upper airway indicate that either shortening the palate or increasing its stiffness may be effective in relieving snoring (Ellis et al. (1994) supra). This hypothesis was supported by the elimination or significant reduction of snoring in 14 of 16 patients treated (Ellis et al. (1994) supra). Patients, however, reported severe soreness of the throat lasting about one week post-procedure. Longer term follow-up revealed some late failures (Ellis et al. (1994) supra), as has been the experience with UPPP. This procedure has also been modified by use of punctate monopolar electrocautery in non-apneic snorers (Whinney et al. (1995) *J. Laryngol. Otol.* 109:849–852). The procedure consists of, under general anesthesia, making ten to fifteen punctures of the soft palate and the palatal muscles diathermized on each puncture. At follow-up two to ten months after surgery, 18 of 21 patients reported improvement in snoring.

U.S. Pat. No. 5,674,191 discloses a method and apparatus for treating snoring using an ablation apparatus with a cannula for insertion of an energy delivery device into the soft palate and uvula. This method may be used to cause shrinkage and stiffening of the soft palate. The method may be used with the patient under local anesthesia, however, insertion of the energy delivery device into the tissues results in a wound on the tissue surface with the associated potential for pain and infection.

It is desirable to cause stiffening of the soft palate for treatment of simple snoring and other forms of sleep-disordered breathing in a manner that is non-invasive and leaves the tissue surface substantially intact, and which can be performed under local anesthesia.

SUMMARY OF THE INVENTION

The present invention provides a non-invasive method for ameliorating the symptoms of sleep-disordered breathing syndromes (e.g., snoring) in a mammal (e.g., a human). The method, referred to as laser soft palate stiffening (LSPS), involves stiffening a preselected region in the soft palate of the mammal and is accomplished while avoiding or minimizing injury to the epithelial tissue of the soft palate.

In its broadest aspect, the non-invasive (i.e., does not require insertion of an energy delivery device into soft palate tissue) method of the invention comprises delivering energy to a preselected tissue region of interest, for which subsurface remodeling is the objective, but minimization of surface damage is desirable. A specific implementation of this is the application of radiation to soft palate tissue in an amount and duration sufficient to induce thermal injury of subepithelial tissue in the preselected region while minimizing thermal injury to epithelial tissue in the preselected region. The thermal injury of the subepithelial tissue results in healing response in the tissue leading to stiffening and/or shrinkage of the preselected region of the soft palate tissue and peripheral tissues.

In one embodiment, minimization of thermal injury to the epithelial tissue is accomplished by cooling the epithelial tissue prior to and/or contemporaneous with the induction of thermal injury to the subepithelial tissue.

In another embodiment, thermal injury of the subepithelial tissue induces fibrosis in the subepithelial tissue of the preselected region of soft palate tissue. In addition, the thermal injury also may result in denaturation of collagen disposed within the subepithelial tissue of the preselected region of soft palate tissue. As a result of fibrosis and/or collagen denaturation, stiffening of the preselected region of soft palate tissue occurs. Implementation of the procedure also may result in shrinkage in surface area of the preselected region of soft palate tissue relative to untreated tissue.

In another embodiment, the energy is provided, for example, by a source of laser light, incoherent light, microwaves, ultrasound or RF current. In a detailed embodiment, the energy is provided via a beam of radiation. The radiation may be pulsed, scanned or gated continuous wave (CW) laser or incoherent radiation. In one embodiment, a laser source provides a beam of radiation having a wavelength in the range from about 0.6 to about 1.8 microns, and more specifically having a wavelength of about 1.5 microns.

Implementation of the method of the invention results in stiffening of the preselected region of the soft palate tissue thereby ameliorating the symptoms of sleep-disordered breathing. In one preferred embodiment, use of the method reduces snoring in an individual susceptible to snoring.

It is contemplated that energy from the energy source also may be used to treat tissue adjacent to the soft palate. As a result, treatment of the adjacent tissue may indirectly induce stiffening in the soft palate thereby ameliorating the symptoms of sleep-disordered breathing.

The foregoing and other objects, features and advantages of the present invention will be made more apparent from the following detailed description of preferred embodiments of the invention.

BRIEF DESCRIPTION OF THE DRAWINGS

The objects and features of the invention may be better understood by reference to the drawings described below, wherein like referenced features identify common features in corresponding drawings.

DETAILED DESCRIPTION OF THE INVENTION

The present invention provides a non-invasive method for ameliorating the symptoms of sleep-disordered breathing in a mammal. The method involves stiffening or shrinkage of one or more preselected regions in the soft palate of the mammal while avoiding or minimizing injury to the epithelial tissue of the soft palate.

The method comprises applying energy to a preselected region of the soft palate tissue in a mammal in an amount and duration sufficient to induce thermal injury of subepithelial tissue in the preselected region while minimizing thermal injury to epithelial tissue in the preselected region. Thermal injury of the subepithelial tissue results in a stiffening of the preselected region of the soft palate tissue thereby reducing snoring in the mammal.

Figure 1:
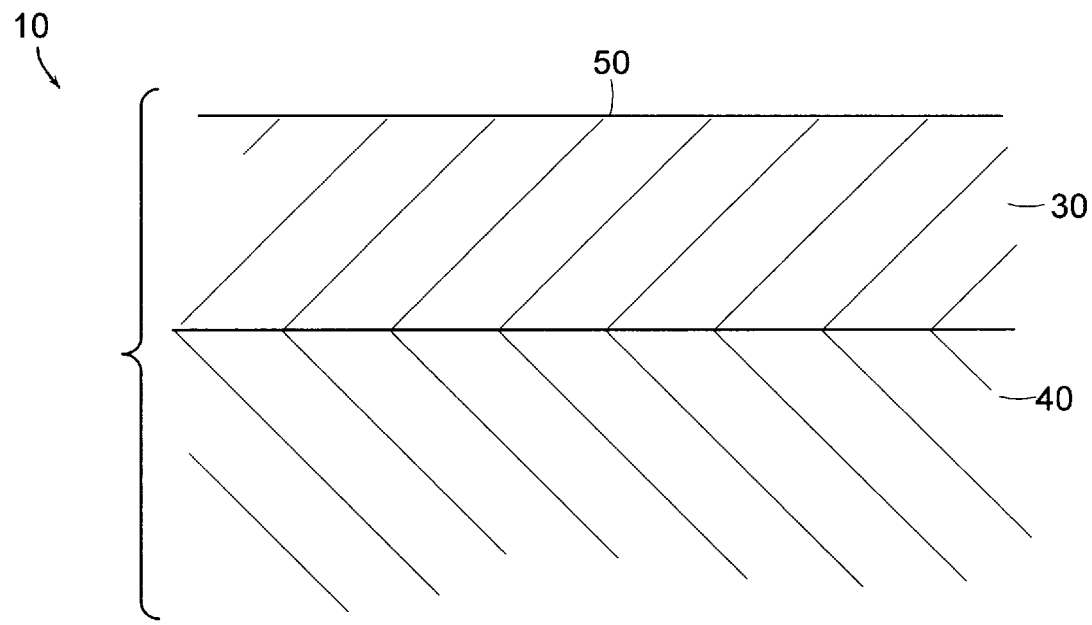
FIG. 1 is a cross-sectional illustration of soft palate tissue.

FIG. 1 is a schematic illustration of a cross sectional view through soft palate tissue 10 in which epithelial tissue 30 is supported upon subepithelial tissue 40. The epithelial tissue 30 has exposed surface 50. As used herein, the term "subepithelial tissue" is understood to mean mucosal connective tissue (lamina propia), submucosa, and may also include adipose and muscle tissue layers. As used herein, the term "epithelial tissue" is understood to mean the non-keratinized stratified squamous epithelium of the soft palate. It is understood that the soft palate tissue also may include the uvula.

As used herein, the term "thermal damage" is understood to mean any tissue damage resulting from exposure to externally provided energy and may range from mild tissue injury sufficient to elicit a healing response to tissue necrosis. As used herein, the term "stiffening" with respect to the preselected region of the soft palate is understood to mean a decrease in elasticity of the preselected region. Stiffening may result from fibrosis and/or collagen denaturation within the subepithelial tissue, or simply may result from a healing response yielding soft palate tissue with improved "tone". Stiffening can be measured by the change in deformation or mechanical compliance in response to an externally applied force. Shrinkage of tissue also may be a desirable outcome and can be quantified by measuring the change in volume of the air passage. Air flow, measured before and after treatment is example of an indirect measure of this remodeling process.

The energy may be provided by any energy source capable of heating living tissue in depth including, for example, a source of laser light, incoherent light, microwaves, ultrasound or RF current. The energy, however, preferably is provided via radiation beam produced by laser and/or incoherent light. Most preferably, the energy is provided by means of laser light which, without limitation, may be produced by a pulsed, scanned or gated CW laser.

With regard to the radiation beam, it is contemplated that the optimal wavelength of the beam may be optimized by routine experimentation to maximize absorption within the subepithelial tissue of the soft palate. The radiation beam preferably has a wavelength in the range from about 0.6 to about 1.8 microns. More specifically, the radiation beam can have a nominal wavelength of about 1.5 microns. Lasers which produce radiation having wavelengths in the range from about 0.6 to about 1.8 microns include, for example, the 0.69 micron ruby laser, the 0.8 micron diode laser, the 1.06 micron Nd:YAG, the 1.33 micron Nd:YAG laser, the 1.44 micron Nd:YAG laser, and the 1.54 micron Er:Glass laser.

In another embodiment, the radiation beam used to thermally injure the subepithelial tissue originates from a compact, handheld device consisting of a diode laser alone or in conjunction with additional apparatus such as an optical fiber, doped in such a way so as to deliver energy at a wavelength and power level so as to be therapeutically effective.

It is contemplated that therapeutically effective dosimitries for pulsed sources of radiation are in the range from about 5 to about 500 joules per square cm. Similarly, it is contemplated that therapeutically effective dosimitries for CW and chopped sources are in the range from about 1 to about 100 watts per square cm.

Minimization of thermal injury to the epithelial tissue of the soft palate tissue can be accomplished by cooling the epithelial tissue prior to and/or contemporaneous with the induction of thermal injury to the subepithelial tissue. Furthermore, cooling can be applied at intervals between heating pulses, if the heating source is pulsed. Cooling may be facilitated by one or more of the following cooling systems, including, without limitation, blowing a cold stream of gas, for example, cold air, or cold $N_2$ or He gas, onto the surface of the soft palate tissue; spraying a cold liquid stream onto the surface of the soft palate tissue; conductive cooling using a cold contact surface which does not interfere with the method of heating, for example, by using a cooled transparent optical material, such as a cooled sapphire tip; or by application of a low boiling point, non-toxic liquid, for example, tetrafluoroethane or chlorodifluoromethane, onto the surface of the soft palate tissue, thereby cooling the tissue surface by evaporative cooling.

Figure 2:
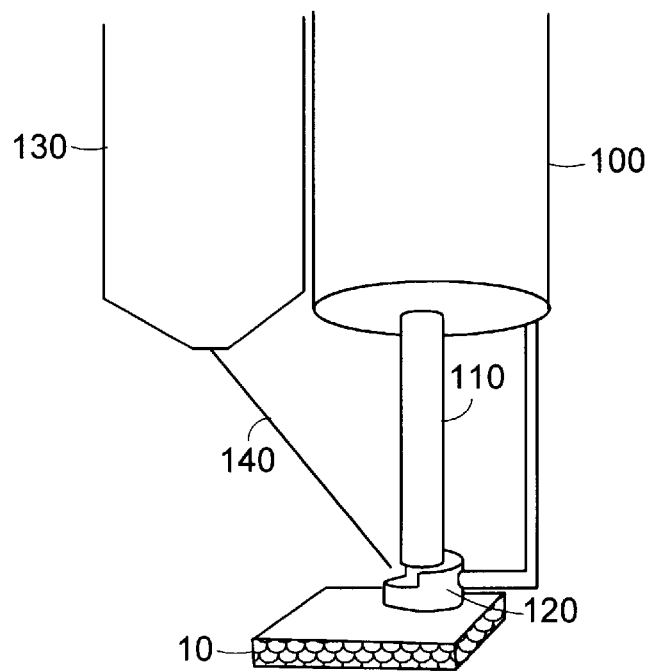
FIG. 2 is an illustration of a delivery system incorporating the principles of the invention.

In one embodiment, the energy delivery and cooling systems comprise separate systems (see, for example, FIG. 2). FIG. 2 shows a detailed embodiment which comprises an energy delivery system 100, for example, a handpiece containing optics for directing, collimating or focusing the radiation beam 110 onto the surface of the soft palate tissue 10. The radiation beam 110 can be carried from the energy source, for example, a laser, to the handpiece by, for example, an optically transparent fiber, for example, an optical fiber. Coolant from separate reservoir 130 is applied to the surface of soft palate tissue 10 via coolant tubing 140. The coolant spray is retained in situ on the surface of the soft palate tissue 10 by ring 120, for example, a transparent ring, which is attached to the energy delivery system 100.

Figure 3:
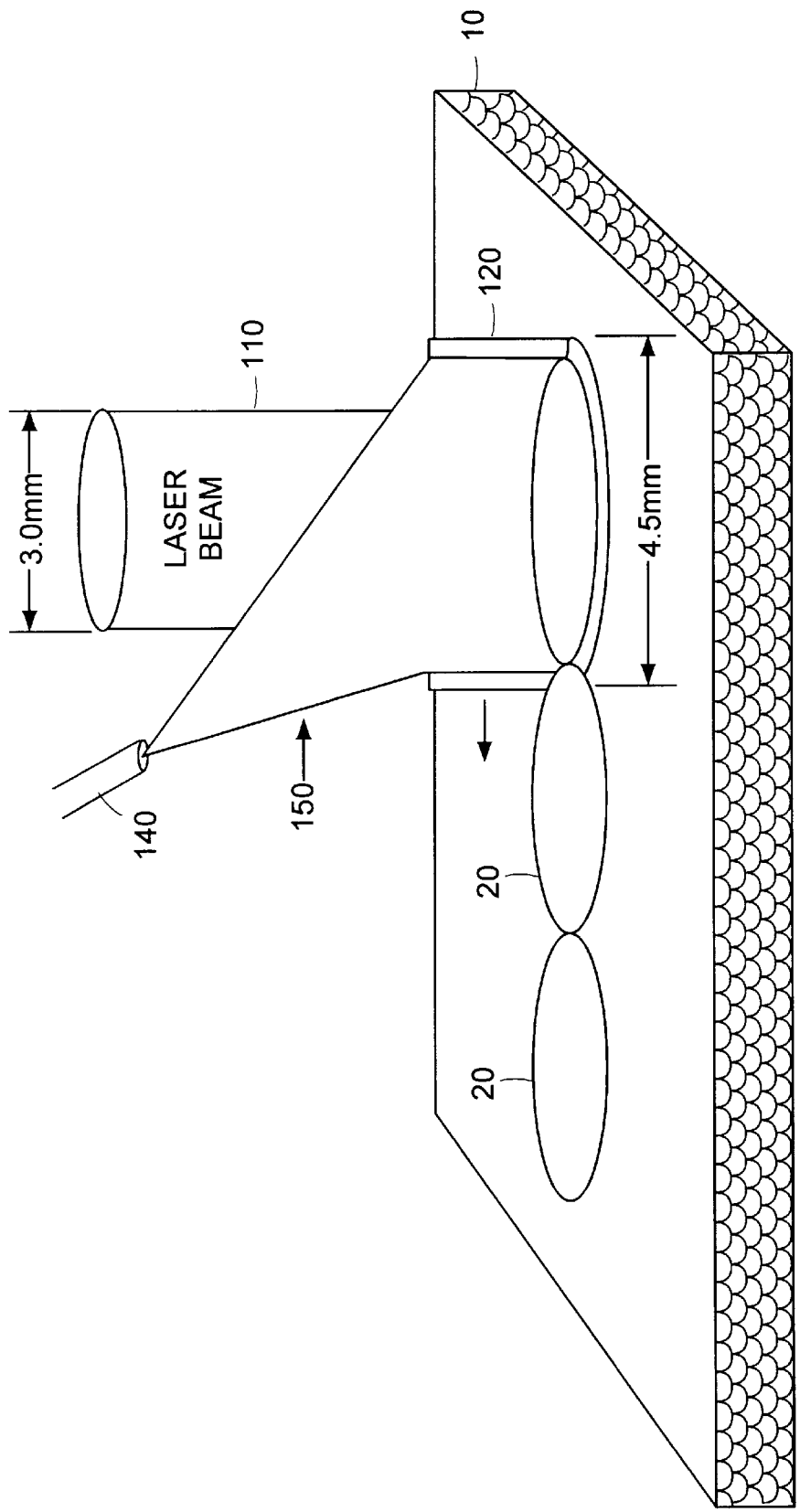
FIG. 3 is a magnified view of the delivery system of FIG. 1. A ring or other device may be used to control or direct the cooling fluid onto the preselected.

Operation of such an embodiment is shown schematically in FIG. 3. Briefly, a preselected region 20 of soft palate tissue 10 is exposed to a radiation beam 110 contemporaneous with the application of cooling spray 150 onto the same preselected region 20 of soft palate tissue 10. The coolant in cooling spray 150 is retained in place by ring 120. Two already irradiated preselected regions 20 also are shown.

In a detailed embodiment, cooling is facilitated by a dynamic cooling device (DCD), such as a DCD manufactured by Candela Corporation. Applications of the DCD device have been described in the art and include, for example, Anvari et al. (1996) *Applied Optics* 35:3314–3319; Anvari et al. (1997) *Phys. Med. Biol.* 42:1–18; Ankara et al. (1995) *Lasers in Medical Science* 10:105–112; and Waldorf et al. (1997) *Dermatol Surg.* 23:657–662, the disclosures of which are hereby incorporated by reference. The DCD works by providing a timed spray of fluid to the surface of the soft palate, prior to the pulse of radiation. Unlike steady-state cooling, for example, an ice cube held against the tissue, dynamic cooling primarily reduces the temperature of the most superficial layers of the soft palate. For example, use of tetrafluoroethane as a cryogen may result in a drop in surface-temperature of about 30–40° C. in about 5–100 ms (see Anvari et al. (1991) supra).

Further, it is contemplated that the energy delivery system 100 also may include an integrated cooling system for cooling the surface of the soft palate prior to and/or during application of the radiation beam. Accordingly, such an energy delivery system would be multi-functional, i.e., capable of both delivering radiation and cooling the surface of the skin at the same time.

In one embodiment, the preselected region is cooled prior to application of the radiation beam. The relative timing of cooling the surface of the soft palate tissue to applying radiation depends, in part, on the depth to which thermal injury is to be prevented. Longer periods of cooling prior to the application of radiation allow more time for heat to diffuse out of the soft palate tissue and cause a thicker layer of soft palate tissue to be cooled, as compared to the thickness of the layer cooled by a short period of cooling. This thicker layer of cooled tissue sustains less thermal injury when the radiation energy is subsequently applied. Continued cooling of the surface of the soft palate tissue during the delivery of radiation energy extracts heat from the upper layers of the soft palate tissue as heat is deposited by the radiation, thereby further protecting the upper layers from thermal injury.

The depth of thermal injury caused by the radiation depends primarily on the penetration depth of the radiation used. The penetration depth can be approximated by taking the reciprocal of the absorption coefficient of the soft palate tissue at the wavelength of the radiation. The thickness of the tissue overlying the zone of injury which is spared from injury depends primarily on the cooling applied prior to and/or during the delivery of radiation energy. By suitably choosing the radiation wavelength, the timing of the surface cooling, the cooling method, the cooling temperature, radiation pulse energies, radiation pulse repetition rates, time intervals of radiation energy delivery, and total number of radiation pulses, the depth, thickness and degree of thermal injury can be confined to a zone of the subepithelial tissue. These parameters can be chosen to optimally induce the injury required to elicit healing within the subepithelial tissue, while substantially or completely sparing injury to the overlying epithelial tissue of the soft palate.

By limiting thermal injury to the subepithelial tissue of the palate while substantially maintaining the integrity of the epithelial tissue, it is contemplated that the method will induce stiffening and/or shrinkage of the soft palate while minimizing the soreness or pain resulting from the procedure and substantially shorten the recovery period.

In one embodiment, an externally injected radiation absorber, for example, a non-toxic dye, such as, Indocynanine Green, can be injected into the subepithelial tissue of the soft palate. A radiation source provides radiation which is well absorbed by the tissue containing absorber. As a result, thermal injury can be confined to the subepithelial tissue and potential injury to the epithelial tissue is minimized.

EXAMPLES

Practice of the invention will be more fully understood from the following examples, which are presented herein for illustrative purposes only, and should not be construed as limiting the invention in any way.

Example 1

The following in vivo experiments on hamsters demonstrate the feasibility of the method of increasing the stiffness of skin tissue without sloughing or otherwise compromising the integrity of epithelial tissue (i.e., superficial epithelial layers) of the skin. This effect is particularly desirable in treatment of soft palate tissue.

In this series of experiments, hamster skin was exposed to a laser beam with or without cooling of the skin surface. From the results discussed herein, it is apparent that the technique causes significant shrinkage and decreased elasticity (stiffening) in hamster skin while preserving the epithelial tissue at the skin surface.

Two Syrian Golden hamsters (Mesocricetus auratus) were used to determine the acute and delayed effect of laser irradiation with and without surface cooling. Four areas, each initially 10 mm×10 mm in size were shaved, marked with India ink, and irradiated with a pulsed erbium glass laser (Candela Corporation, Wayland, Mass.) using 1.2 J and 2 Hz repetition rate via a painting motion. The pulsed erbium glass laser produced radiation having a wavelength of 1.54 microns. Laser radiation was applied to the tissue surface using an optical fiber and handpiece as shown in FIG. 2.

The treatment areas received either (i) no cooling, (ii) cooling by room temperature saline irrigation, (iii) cooling by a 20 ms dynamic cooling pulse proceeding each laser pulse, or (iv) cooling by 40 ms dynamic cooling pulses. The dynamic coolants were applied to the tissue surface immediately prior to each laser pulse by means of a subminature solenoid valve attached to the laser handpiece for application of a brief pulse of tetrafluoroethane (HFC-134a) obtained from ICE KLEA (Wilmington, Del.). HFC-134a is a non-flammable hydrocarbon transparent to the laser radiation, with a boiling point of −26.1° C. When emitted as a room temperature fluid spray, the HFC-134a formed a thin layer of coolant on the tissue surface that cooled the tissue surface by evaporation. HFC-134a typically cools superficial tissue layer to approximately −10° C. The laser pulse was emitted immediately after the end of the coolant spray, when the tissue surface temperature was at a minimum.

The laser beam at the surface of the tissue was approximately 3 mm in diameter. The coolant was emitted at room temperature from a hypodermic tube attached to the solenoid valve and was collected within a transparent ring (approximately 4.5 mm in diameter) attached to the laser handpiece and in contact with the tissue surface. The diameter of the ring was slightly larger than the diameter of the laser beam at the tissue surface.

The animals were observed for 28 days and the condition of the treatment areas noted (see TABLE I). By day 7, all sites with the exception of the 40 ms dynamic cooling showed sloughing. By day 28, sites that had sloughed were reepithelialized. The size of the four areas by day 28 were 8.5 mm×8.0 mm (no cooling), 8.5 mm×8.5 mm (saline cooling), 8.5 mm×8.0 mm (20 ms HFC-134a), and 8.5 mm×8.0 mm (40 ms HFC-134a).

TABLE I

|  | Laser Alone | Saline Irrigation | HFC-134a (20 ms) | HFC-134a (40 ms) |
| --- | --- | --- | --- | --- |
| Acute | blanching | purpura | purpura | purpura |
| Day 1 | purpura | purpura | purpura | normal |
| Day 3 | purpura | purpura | purpura | purpura |
| Day 7 | sloughing | sloughing | sloughing | desquamation |
| Day 14 | reepithelization | reepithelization | reepithelization | hypopigmentation |
| Day 28 | hypopigmentation | hypopigmentation | hypopigmentation | hypopigmentation |

Figure 4:
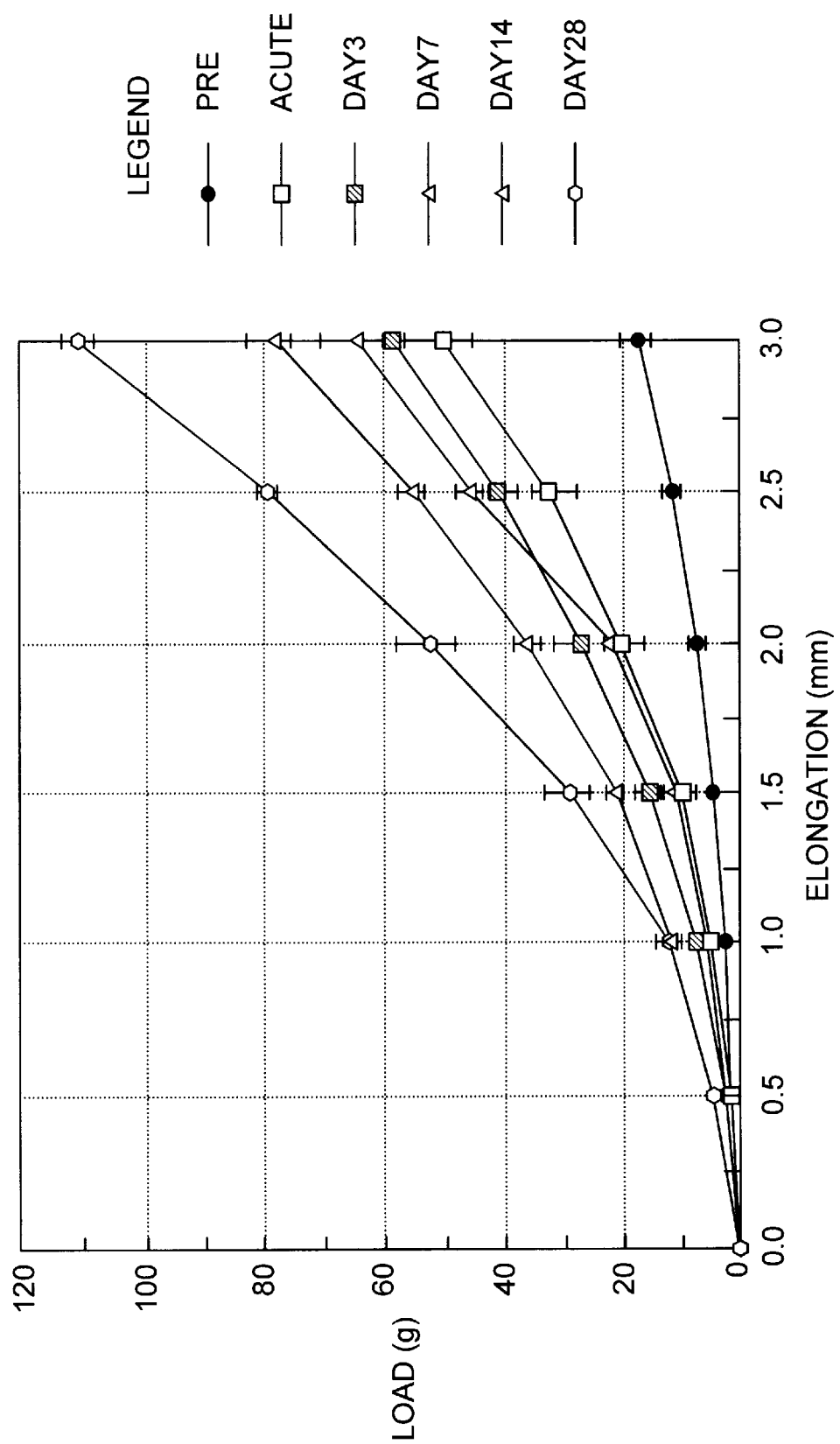
FIG. 4 is a graph illustrating the effect of the method on hamster skin. Load in grams is plotted as a function of elongation (deformation) of the skin, at various points in time after treatment.

The effect of the method on the hamster skin elasticity also was determined, at the site treated with 40 ms HFC-134a cooling. Tensile force measurements on the tissue were performed using a micrometer translation stage, and a load cell (LCL-816G, Omega Engineering, Stanford, Conn.) connected to a personal computer with a data acquisition system. The tensile force measurements were made in vivo immediately, and at days 1, 3, 7, 14, and 28 after irradiation, the results of which are summarized in FIG. 4. FIG. 4 shows in vivo load versus deformation data obtained at various points in time after treatment. The results indicate that skin elasticity decreases with time after treatment, for a period of at least about one month.

In a second set of in vivo hamster skin experiments, the tetrafluoroethane dynamic cooling pulse was fixed at 40 ms (the duration demonstrated to prevent sloughing in skin tissue) and laser parameters were varied. Two hamsters had 6 irradiation sites (A–F), each initially 10 mm×10 mm in size, marked on the skin. All sites were cooled with 40 ms dynamic cooling pulses using the transparent ring shown in FIG. 2 to limit cooling area, with the exception of site E which was cooled without the ring.

TABLE II

| Site | Energy (J) | Duration (s) | Total Energy (J) | Irradiated Area At Day 28 |
| --- | --- | --- | --- | --- |
| A | 0.6 | 15 | 18 | 9.0 mm × 9.0 mm |
| B | 0.8 | 15 | 24 | 9.0 mm × 9.0 mm |
| C | 1.0 | 15 | 30 | 8.5 mm × 8.5 mm |
| D | 1.2 | 15 | 36 | 8.0 mm × 8.0 mm |
| E* | 1.2 | 15 | 36 | 9.5 mm × 9.0 mm |
| F | 1.2 | 40 | 96 | 8.5 mm × 8.0 mm |

The only effect seen at any of sites A–F was purpura. At day 7, there was some delayed desquamation on the tissue surface but no sloughing. There was no notable difference between the 6 sites. At day 28, treated sites appeared hypopigmented but otherwise normal. Tissue shrinkage tended to increase with increasing total energy, with the exception of site E. At that site, each pulse of the cooling spray affected a significantly larger area than the laser spot size, and tissue shrinkage was less.

The aforementioned results indicate that it is possible to induce shrinkage of hamster skin tissue following laser irradiation with surface cooling, without sloughing of tissue. Tissue stiffening appeared acutely and increased postoperatively, for a period of at least about one month, in hamster skin.

Example 2

The hamster provides a useful system model as tissue healing can be readily observed and mechanical properties of the hamster skin easily determined. However, a limitation of the hamster model is that hamster skin is thinner, by virtue of the collagenous tissue layer, than the human soft palate. Accordingly, the hamster experiments were followed up with in vitro canine soft palate experiments because canine soft palates are similar in anatomy to human soft palates.

Figure 5:
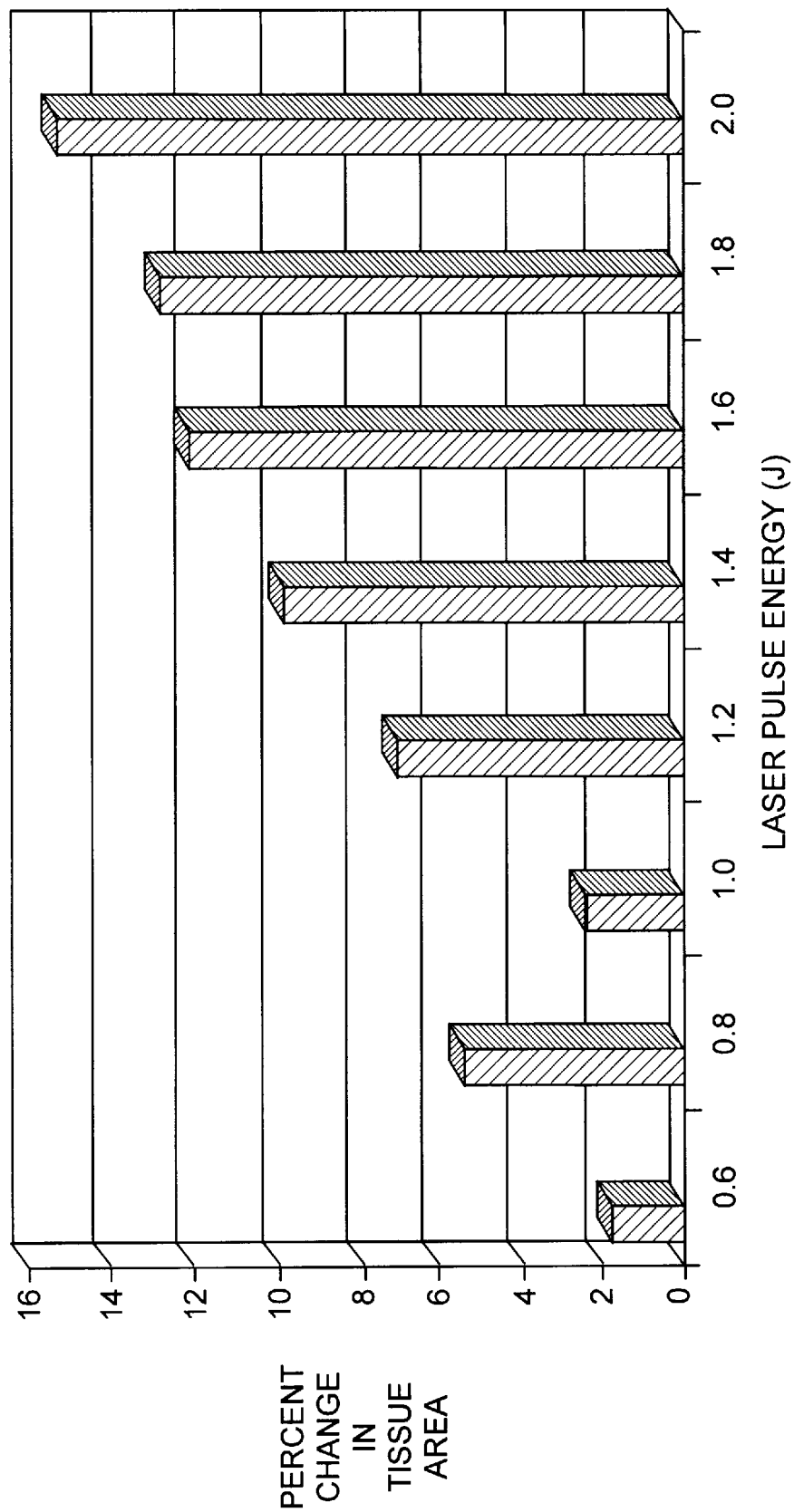
FIG. 5 shows the acute effect of the method on excised canine soft palates. Reduction in surface area is shown as a function of irradiation parameters.

Experiments were performed with fresh samples of canine soft palates excised from animals sacrificed for other purposes. Samples, approximately 10 mm×10 mm were kept moist with saline-soaked gauze until ready for use. All tests were performed with the tissue at physiological temperature (37° C.) in a humified environment. The samples were irradiated using pulse energies of 0.6 to 2.0 J, at 1 Hz repetition rate, and with cooling pulses of 40 ms duration. Tissue shrinkage was measured as a function of laser pulse energy and the results plotted in FIG. 5. As was the case with the hamster skin experiments (Example 1), tissue shrinkage was observed. Tissue shrinkage was determined to increase with increasing pulse energy (FIG. 5).

Additional samples of fresh soft palate tissue for canines were used to determine the depth of thermal damage induced by treatment. As before, the laser was operated at 1 Hz. Three tissue samples were irradiated using the laser parameters summarized in TABLE III. Samples were biopsied and processed for light microscopy using a haemotoxylin and eosin stain. The average depth of thermal damage as a function of laser parameters was determined. According to TABLE III, the average depth of damage ranged from about 0.75 mm to about 1.75 mm.

TABLE III

|  | Depth (mm) | | |
| --- | --- | --- | --- |
|  | Min. (mm) | Max. (mm) | Ave. (mm) |
| 2 J, 1 pulse | N/A | N/A | 1.60 |
| 2 J, 2 pulses | 1.40 | 1.80 | 1.60 |
| 2 J, 4 pulses | 1.30 | 1.80 | 1.50 |
| 1 J, 2 pulses | 0.50 | 1.00 | 0.75 |
| 1 J, 4 pulses | 1.00 | 1.50 | 1.30 |
| 1 J, 8 pulses | 1.00 | 1.60 | 1.30 |
| 0.5 J, 4 pulses | 1.00 | 1.20 | 1.10 |
| 0.5 J, 8 pulses | 1.00 | 1.20 | 1.10 |
| 0.5 J, 16 pulses | 1.50 | 2.00 | 1.75 |

The canine soft palate experiments confirmed the acute results obtained in hamster skin, namely that the method induces significant tissue shrinkage. With healing, irradiated soft palate may be expected to fibrose where thermally damaged. The histological results indicate that thermal damage extended from the mucosa into submucosal tissue. It is contemplated that this is a desirable amount of thermal damage for treating a human soft palate. Furthermore, it is contemplated that other wavelengths within the range of 0.6 microns to 1.8 microns may provide deeper zones of thermal damage, for fibrosis and stiffening of underlying musculature, if desirable in some cases.

Equivalents

The invention may be embodied in other specific forms without departing from the spirit or essential characteristics thereof The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for stiffening a preselected region of soft palate tissue comprising epithelial tissue supported by subepithelial tissue in a mammal, the method comprising the steps of:
   (a) cooling an exposed surface of epithelial tissue in the preselected region of soft palate tissue; and
   (b) applying energy to the preselected region of the soft palate tissue to induce thermal injury of the subepithelial tissue in the preselected region, wherein the thermal injury of the subepithelial tissue results in stiffening of the preselected region of the soft palate tissue.

2. The method of claim 1 wherein cooling step (a) is contemporaneous with inducing thermal injury of the subepithelial tissue.

3. The method of claim 1 wherein cooling step (a) is prior to inducing thermal injury of the subepithelial tissue.

4. The method of claim 2 wherein cooling step (a) is prior to inducing thermal injury of the subepithelial tissue.

5. The method of claim 1, wherein in step (b) the thermal injury of the subepithelial tissue induces fibrosis in the subepithelial tissue.

6. The method of claim 1, wherein in step (b) the thermal injury of the subepithelial tissue induces shrinkage of the preselected region of the soft palate tissue.

7. The method of claim 1, wherein in step (b) the stiffening of the preselected region of the soft palate tissue reduces snoring in the mammal.

8. The method of claim 1, wherein in step (a) the energy is provided by laser light, incoherent light, microwaves, ultrasound or RF current.

9. The method of claim 1 wherein in step (a) the energy is provided by laser light.

10. The method of claim 1, wherein the mammal is a human.

11. A non-invasive method for stiffening a preselected region of soft palate tissue comprising epithelial tissue supported by subepithelial tissue in a mammal, the method comprising the steps of:
   (a) providing a radiation beaen having a wavelength in the range from about 0.6 to about 1.8 microns and either a fluence in the range from about 5 to about 500 joules per square cm or a power density in the range from about 1 to about 100 watts per square cm;
   (b) cooling an exposed surface of epithelial tissue in the preselected region of soft palate tissue; and
   (c) applying the beam to the preselected region of the soft palate tissue to induce thermal injury of the subepithelial tissue in the preselected region, wherein the thermal injury of the subepithelial tissue results in stiffening of the preselected region of the soft palate tissue.

12. The method of claim 11, wherein in step (a) the wavelength is about 1.5 microns.

13. The method of claim 11 wherein cooling step (b) is contemporaneous with inducing thermal injury of the subepithelial tissue.

14. The method of claim 11 wherein cooling step (b) is prior to inducing thermal injury of the subepithelial tissue.

15. The method of claim 13 wherein cooling step (b) is prior to inducing thermal injury of the subepithelial tissue.

16. The method of claim 11, wherein in step (c) the thermal injury of the subepithelial tissue induces fibrosis in the subepithelial tissue.

17. The method of claim 11, wherein in step (c) the thermal injury of the subepithelial tissue induces shrinkage of the preselected region of the soft palate tissue.

18. The method of claim 11, wherein in step (c) the stiffening of the preselected region of the soft palate tissue reduces snoring in the mammal.

19. The method of claim 11 comprising the additional step of providing a radiation absorbing material to the subepithelial tissue in the preselected region prior to application of the beam of radiation.

20. The method of claim 11, wherein the mammal is a human.

* * * * *

UNITED STATES PATENT AND TRADEMARK OFFICE
CERTIFICATE OF CORRECTION

PATENT NO.    : 6,026,816
DATED         : February 22, 2000
INVENTOR(S)   : McMillan et al.

It is certified that error appears in the above-identified patent and that said Letters Patent is hereby corrected as shown below:

Title page,
Item [56], add OTHER PUBLICATIONS and under this heading the following articles.
-- Anvari et al., "Nd: YAG laser irradiation in conjunction with cryogen spray cooling induces deep and spatially selective photocoagulation in animal models," *Phys. Med. Biol.* 42:1-18, 1997. --.

-- Anvari et al., "Spatially selective photocoagulation of biological tissues: feasibility study utilizing cryogen spray cooling," *Applied Optics* 35:3314-3320, 1996. --.

-- Anvari et al., "Dynamic Epidermal Cooling in Conjunction with Laser Treatment of Port-Wine Stains: Theoretical and Preliminary Clinical Evaluations," *Lasers in Medical Science* 10:105-112, 1995. --.

-- Breslau et al., "Daytime Sleepiness: An Epidemiological Study of Young Adults," *Am. J. Public Health* 87:1649-1653, 1997. --.

-- Croft et al., "Uses and complications of uvulopalatopharyngoplasty," *J. of Laryngology and Otology* 104:871-875, 1990. --.

-- Ellis, P.D.M., "Laser palatoplasty for snoring due to a palatal flutter: a further report," *Clin. Otolaryngol.*, 19:350-351, 1994. --.

-- Ellis et al., "Surgical relief of snoring due to palatal flutter: a preliminary report," *Ann. Roy. Coll. Surg. Engl.* 75:286-291, 1993. --.

-- Friberg et al., "UPPP for Habitual Snoring: A 5-Year Follow-up With Respiratory Sleep Recordings," *Laryngoscope* 105:519-522, 1995. --.

-- Friberg et al., "Habitual Snorers and Sleep Apnoics Have Abnormal Vascular Reactions of the Soft Palatal Mucosa on Afferent Nerve Stimpulation," *Laryngoscope* 108:431-436, 1998. --.

-- Gnuechtel et al., "Electrocautery Versus Carbon Dioxide Laser for Uvulopalatoplasty in the Treatment of Snoring," *Laryngoscope* 107:848-854, 1997. --.

-- Guilleminault et al., "Upper Airway Resistance Syndrome, Nocturnal Blood Pressure Monitoring, and Borderline Hypertension," *Chest* 109:901-908, 1996. --.

-- Hanada et al., "Laser-Assisted Uvulopalatoplasty With Nd: YAG Laser for Sleep Disorders," *Laryngoscope* 106:1531-1533, 1996. --.

UNITED STATES PATENT AND TRADEMARK OFFICE
CERTIFICATE OF CORRECTION

PATENT NO. : 6,026,816
DATED : February 22, 2000
INVENTOR(S) : McMillan et al.

It is certified that error appears in the above-identified patent and that said Letters Patent is hereby corrected as shown below:

-- Harries et al., "The Surgical Treatment of Snoring," *J. of Larngology and Otology* 110:1105-1106, 1996. --

-- Kamami, Y., "Outpatient Treatment of Snoring with $CO_2$ Laser: Laser-Assisted UPPP," *J. of Otolaryngology* 23:391-395, 1994. --.

-- Lofaso et al., "Sleep Fragmentation as a Risk Factor for Hypertension in Middle-aged Nonapneic Snorers," *Chest* 109:896-900, 1996. --.

-- Lauretano et al., "Efficacy of Laser-assisted Uvulopalatoplasty," presented at the Sixteenth Annual Meeting of the American Society for Laser Medicine and Suregery in Orlando, Florida on April 16, 1996. --.

-- Maycock, G., "Sleepiness and driving: the experience of UK car drivers," *J. Sleep Res.* 5:229-237, 1996. --.

-- McMillan et al., "Laser Soft Palate Stiffening," presented at the Lasers and Optical Technology in Otolaryngology Conference, Conference 3245-25, January 24, 1998. --.

-- Ohayon et al., "Snoring and breathing pauses during sleep: telephone interview survey of a United Kingdom population sample," BMJ 314:860-863, 1997. --.

-- Spriggs et al., "Effect of the risk factors for stroke on survival," *Neurological Research* 14:94-96, 1992. --.

-- Stradling, J.R. et al., "Self reported snoring and daytime sleepiness in men aged 35-36 years," *Thorax* 46:807-810, 1991. --.

-- Utley et al., "A Cost-Effective and Rational Surgical Approach to Patients With Snoring, Upper Airway Resistance Sydrome, or Obstructive Sleep Apnea Syndrome," *Laryngoscope* 107:726-734, 1997. --.

-- Waldorf et al., "Effect of Dynamic Cooling on 585-nm Pulsed Dye Laser Treatment of Port-Wine Stain Birthmarks," *Dermatol. Surg.* 23:657-662, 1997. --.

-- Walker et al., "Laser-Assisted Uvulopalatoplasty for Snoring and Obstructive Sleep Apnea: Results in 170 Patients," *Laryngoscope* 105:938-943, 1995. --.

-- Wareing et al., "Laser-assisted uvulopalatoplasty: an assessment of a technique," *J.of Laryngology and Otology* 110:232-236, 1996. --.

UNITED STATES PATENT AND TRADEMARK OFFICE
CERTIFICATE OF CORRECTION

PATENT NO. : 6,026,816
DATED : February 22, 2000
INVENTOR(S) : McMillan et al.

It is certified that error appears in the above-identified patent and that said Letters Patent is hereby corrected as shown below:

-- Whinney et al., "Punctate diathermy of the soft palate: a new approach I the surgical management of snoring," *J. of Laryngology and Otology* 109:849-852, 1995. --.

-- Boot et al., "Uvulopalatopharyngoplasty for the obstructive sleep apnea syndrome: value of polysomnography, Mueller manoeuvre and cephalometry in predicting surgical outcome," *Clin. Otolaryngol.* 22, 504-510, 1997. --.

-- Millman et al., "The Efficacy of Oral Appliances in the Treatment of Persistent Sleep Apnea After Uvulopalatopharyngoplasty," *Chest*, 113(4), 992-996, April 1998. --.

-- Coleman, Jack A., "Laser-Assisted Uvulopalatoplasty: Long-Term Results with a Treatment for Snoring," *Ear, Nose & Throat Journal*, pp. 22-34, January 1998. --.

-- Finkelstein et al., "Uvulopalatopharyngoplasty vs. Laser-Assisted Uvulopalatoplasty," *Arch Otolaryngol Head Neck Surg.*, 123:265-276, 1997. --.

-- Laranne et al., "Histological changes in elastic components of soft palate scars after $CO_2$ and contact Nd: YAG laser incisions in the dog as an experimental model," *Eur. Arch Otorhinolaryngol* 253:454-459, 1996. --.

-- Yardley et al., "How We Do It: Diathermy Palatoplasty," *J. of Otolaryngology*, 26(4): 284-285, November 4, 1997. --.

-- Schwartz et al., "Effects of electrical stimulation to the soft palate on snoring and obstructive sleep apnea," *J. of Prosthetic Denistry*, 76(3):273-281, September 1996. --.

Column 10, claim 11,
Line 21, delete the word "beaen" and replace with -- beam --

Signed and Sealed this

Twenty-seventh Day of November, 2001

*Attest:*

*Attesting Officer*

NICHOLAS P. GODICI
*Acting Director of the United States Patent and Trademark Office*